United States Patent
Sinha

(10) Patent No.: US 10,760,060 B2
(45) Date of Patent: Sep. 1, 2020

(54) INJECTION AND INCUBATION OF CIRCULATING TUMOR CELLS FROM A CANCER BIOPSY IN ZEBRAFISH FOR ACCELERATED PREDICTION OF CANCER PROGRESSION AND RESPONSE TO TREATMENT

(71) Applicant: BIOMEDCORE, INC., Tecumseh (CA)

(72) Inventor: Indrajit Sinha, Windsor (CA)

(73) Assignee: BIOMEDCORE INC., Tecumseh (CA)

( * ) Notice: Subject to any disclaimer, the term of this patent is extended or adjusted under 35 U.S.C. 154(b) by 827 days.

(21) Appl. No.: 14/649,196

(22) PCT Filed: Dec. 2, 2013

(86) PCT No.: PCT/IB2013/060580
§ 371 (c)(1),
(2) Date: Jun. 2, 2015

(87) PCT Pub. No.: WO2014/083555
PCT Pub. Date: Jun. 5, 2014

(65) Prior Publication Data
US 2015/0315546 A1 Nov. 5, 2015

Related U.S. Application Data

(60) Provisional application No. 61/732,375, filed on Dec. 2, 2012.

(51) Int. Cl.
| | |
|---|---|
| *C12N 5/09* | (2010.01) |
| *C12N 15/02* | (2006.01) |
| *G01N 33/50* | (2006.01) |
| *C12Q 1/6886* | (2018.01) |

(52) U.S. Cl.
CPC .......... *C12N 5/0693* (2013.01); *C12N 15/02* (2013.01); *C12Q 1/6886* (2013.01); *G01N 33/5011* (2013.01); *G01N 33/5088* (2013.01); *C12Q 2600/106* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01); *G01N 2333/43526* (2013.01); *G01N 2800/7028* (2013.01)

(58) Field of Classification Search
CPC ...... C12N 5/0693; C12N 5/02; C12Q 1/6886; G01N 33/5011; G01N 33/5088
See application file for complete search history.

(56) References Cited

U.S. PATENT DOCUMENTS

| | | |
|---|---|---|
| 7,339,090 B2 | 3/2008 | Christmann |
| 7,390,648 B1 | 6/2008 | Palacios-Boyce |
| 8,194,243 B2 | 6/2012 | O'Connell |
| 2005/0112030 A1 | 5/2005 | Gaus |
| 2006/0010510 A1 | 1/2006 | Christmann |
| 2013/0071873 A1 | 3/2013 | Sonneville |

FOREIGN PATENT DOCUMENTS

| | | |
|---|---|---|
| EP | 1870451 A1 | 12/2007 |
| WO | 2002058847 A2 | 8/2002 |

OTHER PUBLICATIONS

Konantz et al., (Ann N Y Acad Sci. Aug. 2012;1266:124-37).*
Spaink et al., (Methods. 2013;62:246-254).*
Carvalho et al., (PLoS One. Feb. 16, 2011. 6(2):e16779 (8 pages).*
Taylor et al., (Zebrafish. 2009;6(4):339-346) (Year: 2009).*
Drummond et al., (Methods in Cell Biology, vol. 100. Chapter 9.2010: pp. 245-346) (Year: 2010).*
Marques et al., (BMC Cancer. 20099:128. 14 pages) (Year: 2009).*
Konantz et al., (Ann N Y Acad Sci;. Aug. 2012;1266:124-37) (Year: 2012).*
Marques, Ines J., et al. "Metastatic behaviour of primary human tumours in a zebrafish xenotransplantation model." BMC cancer 9.1 (2009): 128.*
Zheng, Siyang, et al. "3D microfilter device for viable circulating tumor cell (CTC) enrichment from blood." Biomedical microdevices 13.1 (2011): 203-213.*
Rai, Kunal, et al. "DNA demethylation in zebrafish involves the coupling of a deaminase, a glycosylase, and gadd45." Cell 135.7 (2008): 1201-1212.*
Konantz, "Zebrafish xenografts as a tool for in vivo studies on human cancer." Annals of the New York Academy of Sciences 1266:24-137 Aug. 1, 2012.
Powell, "Single cell profiling of circulating tumor cells: transcriptional heterogeneity and diversity from breast cancer cell lines." PLOS One 7(5):1-11 May 1, 2012.
International Search Report in PCT/IB2013/060580 dated Mar. 31, 2014.
Written Opinion of the International Searching Authority in PCT/IB2013/060580 dated Mar. 31, 2014.
Balic, "Circulating Tumor Cells: From Bench to Bedside." Annual Review of Medicine 64:31-44 Jan. 1, 2003 (epub Oct. 18, 2012).
Cohen, "Prognostic significance of circulating tumor cells in patients with metastatic colorectal cancer." Annals of Oncology 20(7):1223-1229 Jul. 1, 2009 (epub Mar. 12, 2009).
Cristofanilli, "Circulating Tumor Cells, Disease Progression,and Survival in Metastatic Breast Cancer." New England Journal of Medicine 351(8):781-791 Aug. 19, 2004.
Jensen, "PIK3CA Mutations May Be Discordant between Primary and Corresponding Metastatic Disease in Breast Cancer." Clinical Cancer Research 17(4):667-677 Feb. 15, 2011.

(Continued)

*Primary Examiner* — G Steven Vanni
(74) *Attorney, Agent, or Firm* — Henry J. Cittone; Cittone Demers Ameri LLP

(57) ABSTRACT

The present invention provides a method to rapidly screen tumor cells for invasive and metastatic characteristics, heterogeneity and their response to therapeutic agents, and provides a multi-well microinjection system for the automated imaging and microinjection of zebrafish embryos.

18 Claims, 9 Drawing Sheets

(56) References Cited

OTHER PUBLICATIONS

Krebs, "Evaluation and Prognostic Significance of Circulating Tumor Cells in Patients With Non-Small-Cell Lung Cancer." Journal of Clinical Oncology 29(12):1556-1563 Apr. 20, 2011.
Moreno, "Circulating tumor cells predict survival in patients with metastatic prostate cancer." Urology 65(4):713-718 Apr. 1, 2005.
Niikura, "Loss of Human Epidermal Growth Factor Receptor 2 (HER2) Expression in Metastatic Sites of HER2-Overexpressing Primary Breast Tumors." Journal of Clinical Oncology 6(30):593-599 Feb. 20, 2012.
Marques I. J. et al., Metastatic behavious of primary human tumours in a zebrafish xenotransplantation model. BMC Cancer, Apr. 28, 2009, vol. 9, No. 128:1-14.
Lee S. L. C. et al., Hypoxia-induced pathological angiogenesis mediates tumour cell dissemination, invasion, and metastasis in a zebrafish tumour model. PNAS, Nov. 17, 2009, vol. 106, No. 46, pp. 19485-19490.

* cited by examiner

FIG. 1

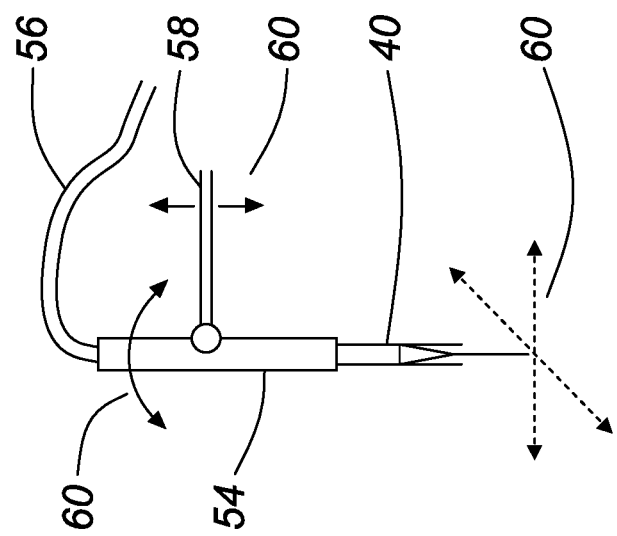
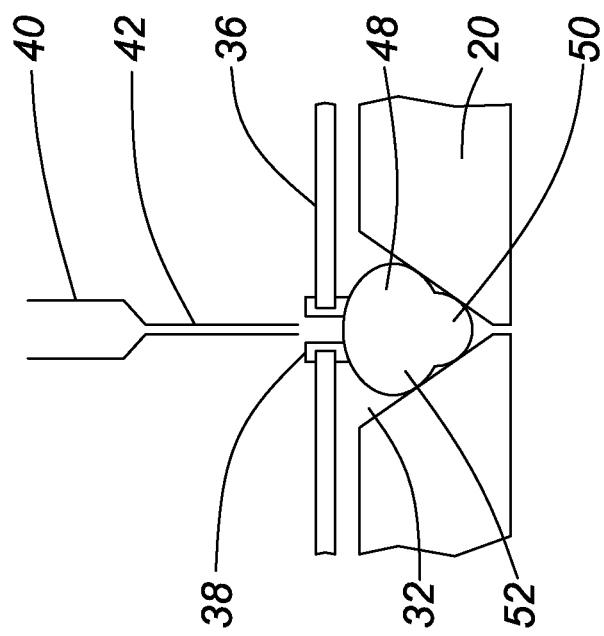
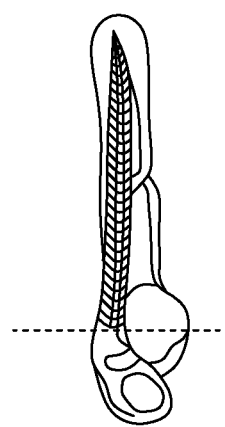
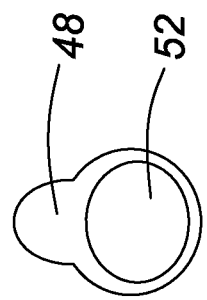
FIG. 8
FIG. 7
FIG. 6A
FIG. 6B

INJECTION AND INCUBATION OF CIRCULATING TUMOR CELLS FROM A CANCER BIOPSY IN ZEBRAFISH FOR ACCELERATED PREDICTION OF CANCER PROGRESSION AND RESPONSE TO TREATMENT

CROSS REFERENCE TO RELATED APPLICATIONS

This application is the U.S. National Stage of PCT/IB2013/060580, filed Dec. 2, 2013, which claims priority to U.S. Provisional Patent Application No. 61/732,375 filed Dec. 2, 2012, the disclosures each of which are incorporated by reference herein in their entirety.

FIELD OF THE INVENTION

The present invention relates to a method of establishing tumors in zebrafish, by injecting human tumor cells. It also relates to the use of the established human tumors in zebrafish for characterizing tumor cells, testing drugs and for individualized medicine. It also relates generally to a multi-well microinjection system and more particularly to a multi-well microinjection system for zebrafish embryos.

BACKGROUND OF THE INVENTION

Proper regulation of signal transduction in cells is responsible for a variety of biological functions including normal cellular replication, growth, cell physiology and cell death. Any perturbations to normal signal transduction in cells can result in various disease states of the body and often disease states are a result of the involvement of more than one cell type and overall body physiology states. Specifically, in the case of cancer, this situation is especially intricate as there is involvement of many underlying inflammatory states of the human body. Diverse inflammatory conditions such as obesity, allergy, arthritis, and diabetes all play a huge role in how cancer progresses and how treatment may work. Therefore, creation of in vivo models that mimic complicated conditions such as cancer require animal models that have an active immune system. Without an active immune system, the dynamic cellular heterogeneity observed in cancer cannot be completely replicated. Furthermore, for clinical usefulness of such animal models of cancer, especially for prediction of the biology of each individual's cancer, organ invasion and cancer cell metastasis to other parts of the body, there should be a way of mimicking an individual patient's cancer in a very short time (before the start of chemotherapy) and predict cancer cell response to treatment.

For epithelial-based cancers, such as cancers of the breast, prostate, lung, colon and pancreas, the need to focus therapy towards such metastasized tumors is of paramount importance. Invasive with distant metastasized stage IV carcinomas present a very low survival rate (seer.cancer.gov).

Metastatic cancer involves the detachment of aggressive malignant cells from the primary tumor into the bloodstream and/or lymphatic channels. Such circulating tumor cells (CTC) manage to reach distant organs where they develop secondary metastasis. Concordantly, the presence of these CTCs is associated with a poor prognosis (Balic M, Williams A, Lin H, Datar R, Cote R J. (2012). Circulating Tumor Cells: From Bench to Bedside. Annu Rev Med. 2012 Oct. 18.).

The treatment of patients with metastatic disease continues to be largely dependent on the information we obtain from the primary tumor in spite of frequent discordance between the biomarkers observed on primary tumors versus those observed on secondary tumors (Naoki Niikura, Jun Liu, Naoki Hayashi, Elizabeth A. Mittendorf, Yun Gong, Shana L. Palla, Yutaka Tokuda, Ana M. Gonzalez-Angulo, Gabriel N. Hortobagyi and Naoto T. Ueno (2011); Loss of Human Epidermal Growth Factor Receptor 2 (HER2) Expression in Metastatic Sites of HER2-Overexpressing Primary Breast Tumors. J Clin Oncol, 30:593-599; Dupont Jensen J, Laenkholm A V, Knoop A, Ewertz M, Bandaru R, Liu W, Hackl W, Barrett J C, Gardner H. (2011); PIK3CA mutations may be discordant between primary and corresponding metastatic disease in breast cancer. Clin Cancer Res. 17:667-77). As the circumstantial originators of secondary tumors and metastasis, understanding the biology of secondary tumors will add new perspectives in the individualized treatment of advanced cancer patients. In support of our hypothesis, the prognostic significance of CTCs has been demonstrated for several types of cancers (Cristofanilli M, Budd G T, Ellis M J, Stopeck A, Matera J, Miller M C, Reuben J M, Doyle G V, Allard W J, Terstappen L W, Hayes D F. (2004); Circulating tumor cells, disease progression, and survival in metastatic breast cancer. N Engl J Med. 351:781-91; Moreno J G, Miller M C, Gross S, Allard W J, Gomella L G, Terstappen L W. (2005); Circulating tumor cells predict survival in patients with metastatic prostate cancer. Urology 65:713-8; Cohen S J, Punt C J, Iannotti N, Saidman B H, Sabbath K D, Gabrail N Y, Picus J, Morse M A, Mitchell E, Miller M C, Doyle G V, Tissing H, Terstappen L W, Meropol N J. (2009); Prognostic significance of circulating tumor cells in patients with metastatic colorectal cancer. Ann Oncol. 20:1223-9; Krebs M G, Sloane R, Priest L, Lancashire L, Hou J M, Greystoke A, Ward T H, Ferraldeschi R, Hughes A, Clack G, Ranson M, Dive C, Blackhall F H. (2011); Evaluation and prognostic significance of circulating tumor cells in patients with non-small-cell lung cancer. J Clin Oncol. 29:1556-63).

Molecular and genomic profiling of cancer cells has become the new trend in targeted therapy and oncology research. However, the relevance of molecular heterogeneity of the cancer cells and their constantly changing nature, the relevance of molecular signatures of the primary tumor as well as the CTCs is limited (Powell A A, Talasaz A H, Zhang H, Coram M A, Reddy A, et al. (2012) Single Cell Profiling of Circulating Tumor Cells: Transcriptional Heterogeneity and Diversity from Breast Cancer Cell Lines. PLoS ONE 7: e33788.).

Molecular and genomic profiling of cancer cells has become important because it can provide targeted therapy for an individual's particular cancer. However, profiling of the primary tumor will not represent the molecular changes that have occurred in the metastatic CTC. What is required for the targeted treatment of metastatic secondary tumors is a way to profile the CTCs.

However there are very few CTCs in a patient's blood so it is very difficult to isolate and characterize the cells. Furthermore, isolating the few CTC in a patient's blood has limited applications, unless the cells can be propagated and examined Growing the CTC in tissue culture may be possible, but in vitro culture does not fully represent the cell characteristics, in particular their ability to invade normal tissues and form three-dimensional tumors, and to recruit growth factors and blood vessels.

The zebrafish, *Danio rerio*, a popular fresh water aquarium fish, is an important model organism and is being increasingly used in scientific research (Lieschke and Currie (2007) "Animal models of human disease: zebrafish swims into view." Nature Reviews Genetics 8:353-367). In medicine, zebrafish has been extremely popular in the study of embryogenesis, cardiovascular research, neuronal development and retinal regeneration but recently it has been established as a great model for almost every kind of cancer as well (Stoletov and Klemke (2008) "Catch of the day: zebrafish as a human cancer model. Oncogene 27:4509-4520)".

Zebrafish are responsive to carcinogenic chemicals and form neoplasms very similar to that seen in humans (Beckwith et al (2000) "Ethylnitrosourea induces neoplasia in zebrafish (*Danio rerio*). Lab Invest. 80(3):379-385). It is also a fantastic model for cancer genetics (Stern and Zon (2003). "Cancer genetics and drug discovery in the zebrafish." Nature Rev. Cancer 3: 533-539). The ease of genetic manipulations in zebrafish has aided its role in being an excellent model for understanding angiogenesis, apoptosis and metastasis (Serbedija et al (1999) "Zebrafish angiogenesis: a novel model for drug screening."; Angiogenesis 3:353-359; Parng et al (2002) "Zebrafish: a preclinical model for drug screening."; Assay Dev. Technol. 1:41-48; Marques et al (2009) "Metastatic behavior of primary human tumours in a zebrafish xenotransplantation model." BMC Cancer 9:128).

Manipulations in zebrafish are performed at various stages of its growth, but 48 hours post fertilization (hpf) is frequently used and is one of the high priority stages for manipulations. The time and manpower required for the processing of many zebrafish embryos during large scale genetic, drug screening and toxicity studies, and cancer cell assays can often be the limiting factor for most laboratories. However, there are presently no commercially available multi-well microinjection systems for 48 hpf zebrafish embryos, primarily because of their elongated and odd shape.

Automated multi-well microinjection systems are well known in the field of cell biology wherein they are primarily used in intranuclear or intracytoplasmic injection of materials such as DNA, RNAi, proteins, or even other cells such as sperm. Automated systems enable a large number of microinjections with reproducible consistency and accuracy that is often hard to achieve manually.

Therefore what is needed to profile and characterize primary tumor cells and CTC is a method to establish and grow the tumor cells in vivo in an animal model. This could allow drug testing on the tumor cells and could provide targeted therapy to the tumor cells in the patient. Furthermore, what is needed in the art is a system that would enable efficient manipulation and injection of 48 hpf zebrafish embryos, for genetic, toxicity, drug, and cancer studies.

BACKGROUND PRIOR ART

Patent Literature

U.S. patent application Ser. No. 10/923,253 (or US2005/0112030A1) filed Aug. 20, 2004 by Stephanie E. Gaus for "Meshwell Plates" which discloses a multiwell plate, such as a 96-well plate, with the bottom tip removed and replaced with a mesh with openings, to allow fast draining of solutions and to prevent "wicking" of solution between wells. The "Meshwell Plate" is stated to be intended to be particularly useful for assaying zebrafish embryos.

PCT Patent Application No. PCT/ES2005/000255 filed May 12, 2005 by Alfonso Gutier-Rez Adan et al for "Supplementation for Embryo and/or Cell Manipulation" which discloses a system for increasing the quality and safety of embryo and cell manipulation media by supplementing the manipulation media with compounds, such as synthetic hyaluronan, phospholipids or unsaturated fatty acids that are obtained from soybeans, to reduce adhesiveness and increase viscosity while retaining the fluidity of the medium, to assist in micromanipulations including microinjection of cells into embryos during preimplantation stage.

U.S. patent application Ser. No. 11/224,364 (or US2006/0010510A1) filed Sep. 12, 2005 by Leandro Christmann for "Microinjection Assembly and Methods for Microinjecting and Reimplanting Avian Eggs" which discloses a microinjection assembly including a microscope, a microinjection system comprising a micromanipulator, a micropipette and a piezo-electric oscillator, and an obliquely angled macro monitoring unit, which allows microinjecting the germinal disk of an avian egg.

PCT Patent Application No. PCT/US2006/0006868 filed Feb. 27, 2006 by Daniel G. O'Connell for "Cell Tray" which discloses a multiwell cell tray that enables automated processing and simultaneous monitoring and analyzing of a large matrix of cells, biological fluids, chemicals and/or solid samples.

U.K. Patent Application No. 1004629 filed Mar. 19, 2012 by Jan De Sonneville for "Array microinjection apparatuses and methods" which discloses an array microinjection apparatus comprising a surface with an array of part-spherical recesses. Each recess can accommodate a single cell or single embryo. An array of injectors matching the recesses holding the cells or embryos may then be used to microinject material into the cells or embryos, especially into the nucleus.

U.S. Pat. No. 7,339,090 patented Mar. 4, 2008 by L. Christmann for "Microinjection Device and Method of Use" which discloses microinjection devices including a needle and a viewing instrument wherein the viewing instrument provides magnified viewing of an object to an operator from an angle other than right angle.

WO 0065137-2000-11-02 by M. Palacios-Boyce for "Microelectromechanical Devices Useful for Manipulating Cells or Embyos" which related to cell labeling microelectromechanical system devices which includes a pair of composite bonded silicon wafers.

WO 2058847-2002-08-01 by M. Paranjape et al for "Cell Transformation Using a Single Chip Silicon Microfabricated Array incorporating Integrated Micro-Piercing Injectors" which provides an improved methodology for the introduction of molecules into cells to provide efficient means for these procedures to be undertaken on a high throughput level.

NON-PATENT LITERATURE 1. seer.cancer.gov
2. Balic M, Williams A, Lin H, Datar R, Cote R J. (2012). Circulating Tumor Cells: From Bench to Bedside. Annu Rev Med. 2012 Oct. 18. [Epub ahead of print]
3. Naoki Niikura, Jun Liu, Naoki Hayashi, Elizabeth A. Mittendorf, Yun Gong, Shana L. Palla, Yutaka Tokuda, Ana M. Gonzalez-Angulo, Gabriel N. Hortobagyi and Naoto T. Ueno (2011). Loss of Human Epidermal Growth Factor Receptor 2 (HER2) Expression in Metastatic Sites of HER2-Overexpressing Primary Breast Tumors. J Clin Oncol, 30:593-599.
4. Dupont Jensen J, Laenkholm A V, Knoop A, Ewertz M, Bandaru R, Liu W, Hackl W, Barrett J C, Gardner H.

(2011). PIK3CA mutations may be discordant between primary and corresponding metastatic disease in breast cancer. Clin Cancer Res. 17:667-77.
5. Cristofanilli M, Budd G T, Ellis M J, Stopeck A, Matera J, Miller M C, Reuben J M, Doyle G V, Allard W J, Terstappen L W, Hayes D F. (2004). Circulating tumor cells, disease progression, and survival in metastatic breast cancer. N Engl J Med. 351:781-91.
6. Moreno J G, Miller M C, Gross S, Allard W J, Gomella L G, Terstappen L W. (2005). Circulating tumor cells predict survival in patients with metastatic prostate cancer. Urology 65:713-8.
7. Cohen S J, Punt C J, Iannotti N, Saidman B H, Sabbath K D, Gabrail N Y, Picus J, Morse M A, Mitchell E, Miller M C, Doyle G V, Tissing H, Terstappen L W, Meropol N J. (2009). Prognostic significance of circulating tumor cells in patients with metastatic colorectal cancer. Ann Oncol. 20:1223-9.
8. Krebs M G, Sloane R, Priest L, Lancashire L, Hou J M, Greystoke A, Ward T H, Ferraldeschi R, Hughes A, Clack G, Ranson M, Dive C, Blackhall F H. (2011). Evaluation and prognostic significance of circulating tumor cells in patients with non-small-cell lung cancer. J Clin Oncol. 29:1556-63.
9. Powell A A, Talasaz A H, Zhang H, Coram M A, Reddy A, et al. (2012) Single Cell Profiling of Circulating Tumor Cells: Transcriptional Heterogeneity and Diversity from Breast Cancer Cell Lines. PLoS ONE 7: e33788.

SUMMARY OF THE INVENTION

Aims of the Invention

The aims of the present invention were to overcome the technical problems of profiling and characterizing primary tumor cells and CTC in an animal model, and to provide a system that would enable efficient manipulation and injection of zebrafish embryos.

The applicant has discovered that these technical problems are solved by way of methods that include creating viable tumors from xeno-transplanted human CTCs into zebrafish, studying the metastatic potential of the injected CTCs, predicting the organ preference of isolated CTCs, and assessing the response to therapeutic agents. A high-throughput accelerated assay method of predicting cancer progression and response to chemotherapy is also presented.

Statement of Invention

In one aspect of the invention, a method is provided to develop three-dimensional tumors from primary tumor cells obtained from biopsies or surgically removed tumors by steps comprising:
(a) Isolating tumor cells
(b) Labeling tumor cells with a cell tracking dye
(c) Injecting the cells into a 24 to 48 hours post fertilization (hpf) zebrafish embryo
(d) Incubating the embryos for 24 hours or more In one embodiment, the tumor cells are obtained from circulating tumor cells (CTCs).

In another embodiment, the cell tracking dye is a fluorescent dye.

In another aspect, the present invention provides a method to predict the likelihood of a primary tumor to invade or metastasize, comprising:
(a) injecting the tumor cells into the yolk of a zebrafish embryo
(b) incubating the embryos with the injected tumor cells
(c) Observing the position of the tumor cells after incubation
(d) analyzing whether the tumor cells (i) invade the body of the embryo through the yolk sac or (ii) whether the cells remain in the yolk sac and behave closely to non-invasive primary tumor cells.

In another embodiment of the invention a method is provided for identifying cancer patients who have a higher probability of disease relapse. The method comprises:
(a) Injecting the primary tumor cells into the yolk of the embryo
(b) Incubating the embryos with the injected tumor cells
(c) Observing the position of the tumor cells after incubation
(d) If the tumor cells enter the body of the embryo, the propensity of the primary tumor to invade and metastasize is high.

In another embodiment, cancer cell invasion may be quantitated by steps comprising:
(a) Isolating tumor cells from a solid tumor
(b) Labeling cells with a cell tracking dye
(c) Micro-injecting the cells into the yolk of a 24-48 hpf zebrafish embryo
(d) Incubating the embryos at 35 degC for 24 h or more.
(e) Capturing automated fluorescent images of the tumor cells under a fluorescent microscope.
(f) Automated analysis of the tumor foci using image analysis software. The data captured are the Width (W) and Length (L) of the tumor foci, the intensity of the signal on each foci, and the position of the spot in the image.
(g) The area of the tumor foci on the captured images provides the size of the foci and volume can be calculated using $\frac{1}{2}WL^2$, where W=Width and L=Length.
(h) Using the position of the tumor foci to measure the propensity of the primary tumor to invade. Invasive Index can be measured as:

Invasion Index (II)=$1/n \, \Sigma$(number of tumor foci in the embryo at T hours/Total number of tumor cells injected in the embryo), where n is the number of embryos considered in the experiment, and T is the incubation time T.
(i) Using the position of the tumor foci can be used to measure the invasive aggressiveness of the tumor. Migration index can be measured as:

Migration Index (MI)=$1/n \, \Sigma$(CD at T hours/Total number of tumor foci at time T hours), where CD=Cumulative distance traveled by tumor cells, n is the number of embryos considered in the experiment, and T is the incubation time.

In another embodiment, a method is provided to measure the response to a chemical by the tumor cells by determining whether any one of: the volume of the tumor foci; the Invasion Index; or the Migration Index are different in the presence versus the absence of said chemical.

In another embodiment of the invention, the prediction of the preferred organ for homing can be made in an automated fashion through image analysis using a transgenic fish with the vascularization fluorescently labeled (such as the Tg(Fli: EGFP)). Based on the vascularization, the location of the tumor foci in the embryo can be predicted. The method comprises:
(a) Isolating tumor cells from a solid tumor
(b) Labeling cells with a cell tracking dye that has red fluorescence such as PKH-26 (Sigma) or DiD (Lifetech).

(c) Micro-injecting the cells into the yolk of a 24-48 hpf Tg(Fli:EGFP) zebrafish embryo.
(d) Incubating the embryos at 35 deg C. for 24 h or more.
(e) Capturing automated fluorescent images of the tumor cells under a fluorescent microscope using filters for both green and red fluorescence.
(f) Automated analysis of the tumor foci using image analysis software. The data captured is the position of the foci in the image.
(g) Image analysis can predict Homing Index of the tumor in an automated fashion and may be calculated as:
Homing Index (HI)=1/n Σ(Total number of foci in an organ at T hours/Total number of tumor foci at time T hours), where n is the number of embryos considered in the experiment, and T is the incubation time T.

In another embodiment, this invention presents a method of monitoring changes in the zebrafish immune system during tumor invasion, metastasis and organ homing processes comprising:
(a) Genetically modified embryos with fluorescent proteins expressed in immune cells may be used to monitor localization and changes in the number of specific immune cells. For example embryos expressing gata2-GFP can be used to monitor localization as well as measure the number of eosinophils present at any part of the zebrafish body.
(b) Whole embryo immuno-histochemical staining of embryos can also be used to locate and enumerate immune cells.

In another aspect of the invention, a method for measuring the number of surviving tumor cells after incubation with or without synthesized or naturally occurring chemicals or biologicals is provided comprising:
(a) Zebrafish embryos are digested in a protease solution
(b) Cells are gently dispersed with pipetting to dissociate the zebrafish embryo to a single cell suspension.
(d) Cells are fixed and counted under a fluorescent microscope.
(e) The ratio of the total number of viable fluorescent tumor cells to the injected number of cells is compared between treated and untreated zebrafish embryos to predict the effect of synthesized or naturally occurring chemicals and biologicals versus untreated embryos In another embodiment, a method is provided to predict drug efficacy against tumor cell invasiveness, comprising measuring and comparing the patterns of invasiveness of tumor cells in the presence or absence of the drug and comparing whether cell invasiveness is different in the presence of the drug.

In another embodiment, a method is provided to predict a drug effect on the organ homing preference of cancer cells through observations of organ-homing pattern change in the absence versus the presence of the drug.

In another aspect of the invention, a method is provided for assessing changes in the DNA of tumor cells comprising:
(a) Enzymatic digestion of whole embryo or part of zebrafish tissues that contain tumor cells
(b) Isolation of DNA from the digested embryo or tissues
(c) PCR amplification of genes of interest using PCR primers designed for human genetic sequences.
(d) Sequencing to locate mutations
(e) Bisulfite sequencing to locate epigenetic modifications In another aspect of the invention, a method is provided to analyze gene expression in cancer cells comprising:
(a) Enzymatic digestion of whole embryo or part of zebrafish tissues that contain tumor cells
(b) Isolation of RNA from the digested embryo or tissues
(c) Quantitative Real-Time PCR analysis of gene expression using specific primers designed for human genetic sequences.

In another aspect of the invention, a method is provided to analyze protein expression in cancer cells comprising one of the following:
(a) Whole embryo is fixed using a chemical fixative such as 4% paraformaldehyde and protein expression may be visualized using immunohistochemistry with specific antibodies to human proteins.
(b) Proteins may be visualized using immunohistochemistry on histological section slides of the zebrafish embryo after injection with tumor cells
(c) Protein expression may be visualized using ELISA (enzyme-linked immunosorption assay) or Western blot.

In another aspect the present invention provides a multi-well microinjection system automating microinjection of 48 hpf zebrafish embryos. The system includes (A) a holding frame; a bottom holding plate supported within the holding frame; and a plurality of removable multi-well modules. Each multi-well module consists of a groove plate and a removable insert. Each groove plate has a plurality of embryo holding wells having conical open bottoms which are arranged in a linear format. Each groove plate has one well module at an outer edge of the groove plate which has a cylindrical shape, thus permitting liquid handling through this well. Each groove plate has a removable insert, having vertical sides and upper circular openings which are aligned with each groove in the groove plate, thus forming an embryo holding and handling well when placed over the top of the groove plate. A lid is provided for covering the holding frame, the groove plate and removable insert. The system also includes (B) a microinjection micropipette rotatably positionable over the multi-well plate for enabling injecting the embryo at variable angles and/or heights.

In another embodiment, the present invention provides a method for the automated microinjection of 24 to 72 hour post-fertilization zebrafish embryos, comprising: placing a plurality of 24 to 72 hour post-fertilization zebrafish embryos in associated ones of multi-well modules of the multi-well microinjection system as particularly described herein and microinjecting a selected molecule into the yolk of the zebrafish embryo.

In another embodiment, the present invention provides a method for causing tumor cells to be efficiently taken up by the zebrafish embryo, comprising microinjecting tumor cells into the yolk of 24 to 72 hour post fertilization zebrafish embryo and either during or after the tumor cells have been microinjected, also microinjecting pro-angiogenic factors, e.g., angiopoietin, into the yolk of the zebrafish embryo, or adding the pro-angiogenic factors, e.g. angiopoietin, into the water in which the zebrafish larvae swim.

In another embodiment, the present invention provides a method for testing drugs for their effect on tumor cells, comprising microinjecting tumor cells into the 24 to 72 hour post-fertilization zebrafish embryo; allowing the tumor to grow within that zebrafish embryo for a predetermined time; microinjecting the drug being tested for its effect on tumor cells into that zebrafish embryo; and monitoring the effect of that drug on the tumor cells by measuring the amount of tumor cell.

Variants of the Invention

Variants of the multi-well microinjection system aspect of this invention include the following: the plurality of embryo holding wells are each interconnected at their open conical bottom to the bottom of the well module at an outer edge of the groove plate;

the automation of the microinjection is performed using a robotic arm controlled micropipette holder;

the automation of the microinjection is performed using a micropipette unit which is controlled by a robotic arm;

the micropipette injection system is structured and arranged to be rotatably positionable, thereby to inject the embryo at variable angles and/or heights;

the position and and/or angle of the robotic arm is adjustable, either manually or according to a commercially-available software-controlled interface, or through the development of a specific automatic injection system which is specifically designed for microinjection into zebrafish embryos;

the robotic arm is controlled through human vision recognition of embryo structures or through vision recognition of embryo structures by means of fluorescence labelling of the cells, or by means of software which is programmed to enable detection of the success of injection of liquids, the software being either commercially-available software-controlled interface, or through the development of a specific automatic injection system which is specifically designed for microinjection into zebrafish embryos;

automation for the selection of the sites of injection and the protocols of injection is changed by software updates; and the automatic microinjection system is controlled by commercially-available microinjector injection system, or through the development of a specific automatic injection system which is specifically designed for microinjection into zebrafish embryos.

A variant of the method for testing drugs for their effect on tumor cells aspect of this invention includes microinjecting tumor cells into the 24 to 72 hour post-fertilization zebrafish embryo, either with or without prior injection of the tumor cells with a stain e.g. the lipophilic fluorescent stain, DiO, and either before, during or after such microinjection of tumor cells into the zebrafish embryo, also microinjecting a pro-angiogenic factor, e.g., the growth factor angiopoietin into the embryo of the 24 to 72 hour post-fertilization zebrafish embryo, or adding the pro-angiogenic factor to the water in which the larvae swim.

OTHER FEATURES OF THE INVENTION

The apparatus can be used with the holding frame and the groove plates in place, without the removable insert, thereby allowing the embryos to rest in the groove of the groove plate but to be accessible by a micropipette for microinjection at variable angles. In this configuration, a removable injection cover plate which has rubber lined apertures over each conical well which is formed by the groove plate, may be placed onto the groove plate and may be used to guide injection of the 48 hour post-fertilization zebrafish embryos.

This invention also provides an option of controlling the robotic arm through vision recognition of embryo structures. In such cases, the software can be designed to enable detection of the success of injection if liquids or labeled cells are fluorescent. Automation for the selection of the sites of injection and the protocols of injection can also be changed by simple software updates. Automation through a visual recognition system will also enable using smaller number of embryos and empty wells.

The apparatus described herein can also be used with manual microinjectors available commercially. Even for manual manipulations, this equipment will reduce labor by reducing extra handling and labeling of tubes. Since embryos are not removed from their wells, the chances of mixing and mislabeling of embryos, as well as inducing stress into the embryos, is greatly reduced.

Changing liquid in the wells when there is a live embryo in it cannot be performed using a robotic arm. However, the ability to change media in one well where there is no living embryo inside, makes the use of a robotic arm feasible. Also, manually changing liquid in wells with a living embryo can be very stressful for the embryo. By this method, gradual change of solution from the well module at an outer edge of the groove plate, which has a cylindrical shape can reduce unnecessary stress on the embryos.

This invention not only provides ease of handling large number of embryos for microinjecting liquids and cells, but it also enables proper positioning and injection of tumor pieces into the embryo in a high throughput fashion.

The multi-well microinjection system described herein, is economical and can be manufactured in a "one time use" fashion.

The multi-well microinjection system and the method of use described herein greatly simplifies handling of a large number of embryos and improves injection accuracies and consistencies over a large number of experiments. Since all wells in a single module are connected, all embryos get the same treatment. Unequal loss of media volume due to drying, or unequal adding per well, does not cause any variation from well to well. Embryos of the same treatment group are exposed to such changes all equally.

This multi-well microinjection system in its preferred embodiment is for use in a 96 well format, but this system can be modified for 6 well, 12 well or 24 well plate formats as well.

This multi-well microinjection system in its preferred embodiment is for use with 48 hour post-fertilization zebrafish embryos, but can also be appropriated for manipulation of 24 to 72 hour post-fertilization zebrafish embryos, for manipulation of embryos from other species of fish, e.g. Medaka, and for embryos from *Xenopus*, rodent, dog, and other laboratory animals.

BRIEF DESCRIPTION OF THE DRAWINGS

In the accompanying drawings:

FIG. 1A: Tumor coordinates of 30 xenografts captured through imaging are represented graphically.

FIG. 1B: Tumor coordinates of 28 xenografts treated with Paclitaxel.

FIG. 1C: Tumor coordinates of 29 xenografts treated with Paclitaxel and Carboplatin. (−D=No drug control, +P=Treated with Paclitaxel, C+P=Treated with Carboplatin and Paclitaxel)

FIG. 1D: Calculated Migration Index of untreated and treated xenografts. (−D=No drug control, +P=Treated with Paclitaxel, C+P=Treated with Carboplatin and Paclitaxel)

FIG. 1E: Calculated Invasion Index of untreated and treated xenografts. (−D=No drug control, +P=Treated with Paclitaxel, C+P=Treated with Carboplatin and Paclitaxel)

FIG. 1F: Brain metastatic tumors were observed in the xenografts, recapitulating the organ-homing observed in the patient.

FIG. 1G: Drug response of the brain metastasis tumors in xenografts. (−D=No drug control, +P=Treated with Paclitaxel, C+P=Treated with Carboplatin and Paclitaxel.

FIG. 1H: Drug response of invasive and non-invasive cells in xenografts treated with Paclitaxel. Drug response was measured through expressions of MGMTs, 9 for survival and 9 for death.

FIG. 1I: Drug response of invasive and non-invasive cells in xenografts treated with Paclitaxel and Carboplatin.

FIG. 6A is a horizontal cross-section view of a 48 hpf zebrafish embryo, and FIG. 6B is a transverse cross-section view of a 48 hpf zebrafish embryo.

FIG. 7 is a schematic side view of the arrangement of a 48 hpf zebrafish embryo in the groove plate with an injection cover plate and a micropipette for microinjection of the embodiment of FIG. 2;

FIG. 8 is a schematic side view of a rotatable micropipette for microinjection of the embodiment of FIG. 2;

DETAILED DESCRIPTION OF THE INVENTION

Introduction

Figure 1:
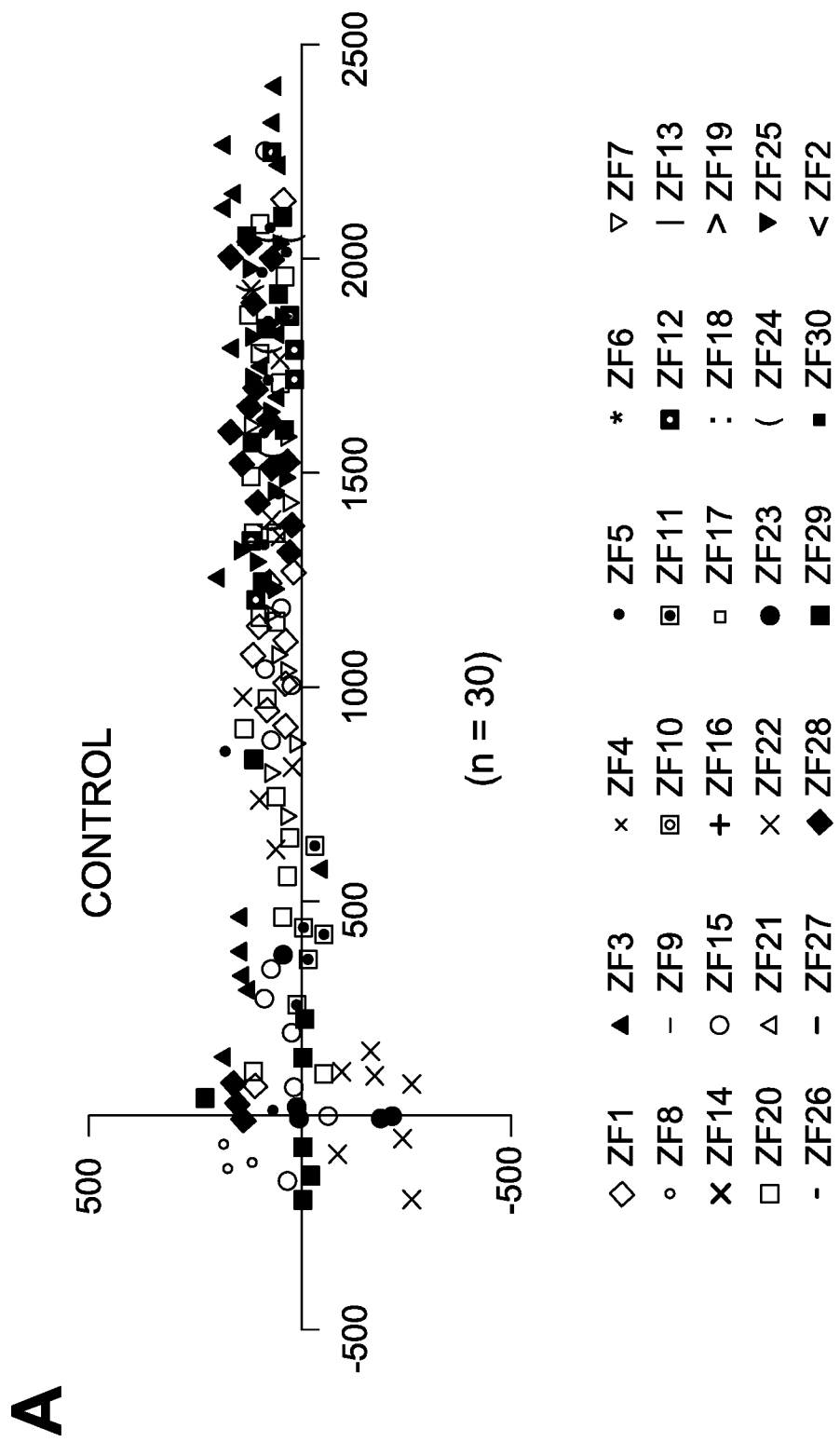
FIG. 1: Differential response of invasive and non-invasive primary lung tumor cells to drugs.
Figure 1:
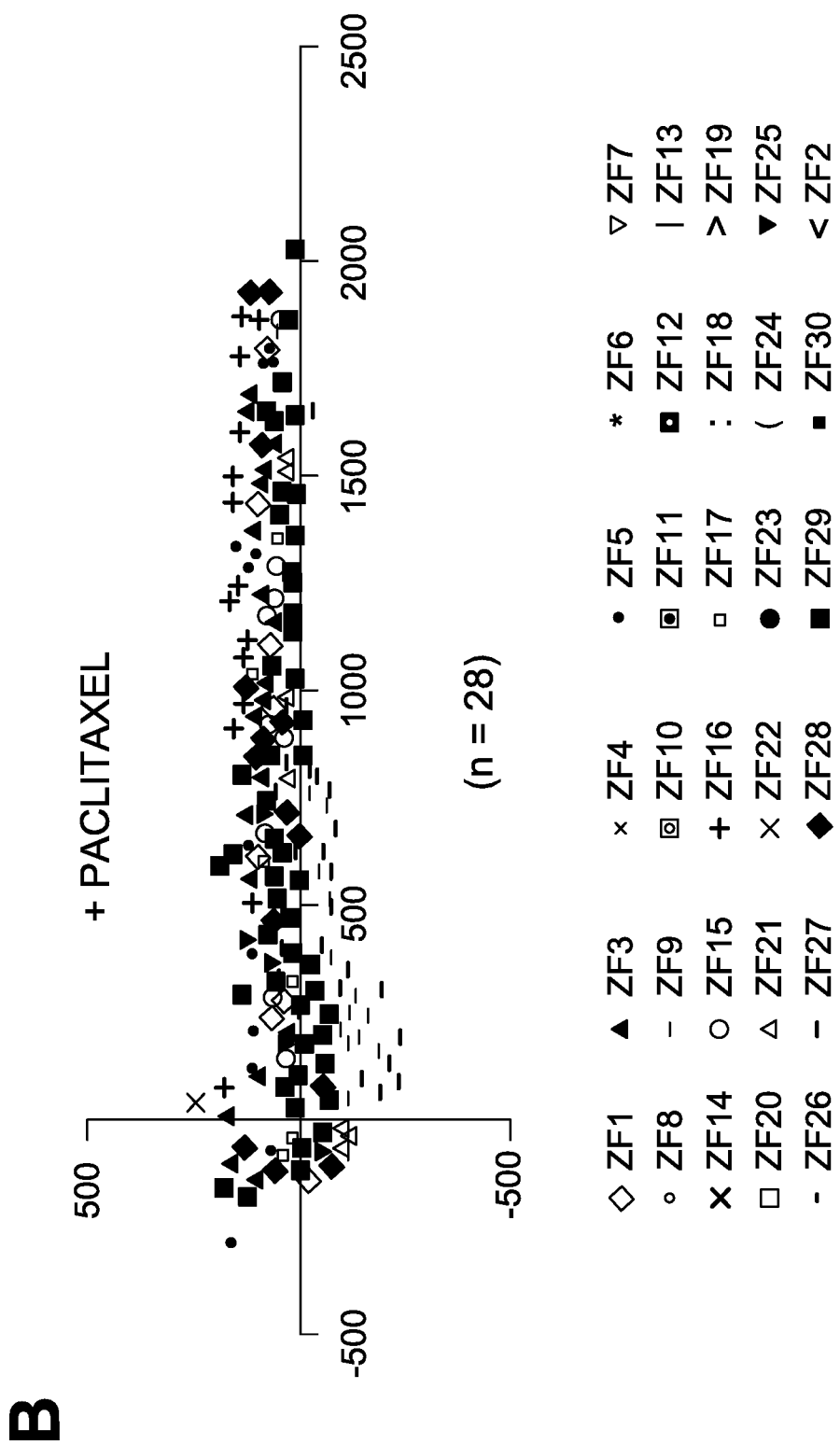
Figure 1:
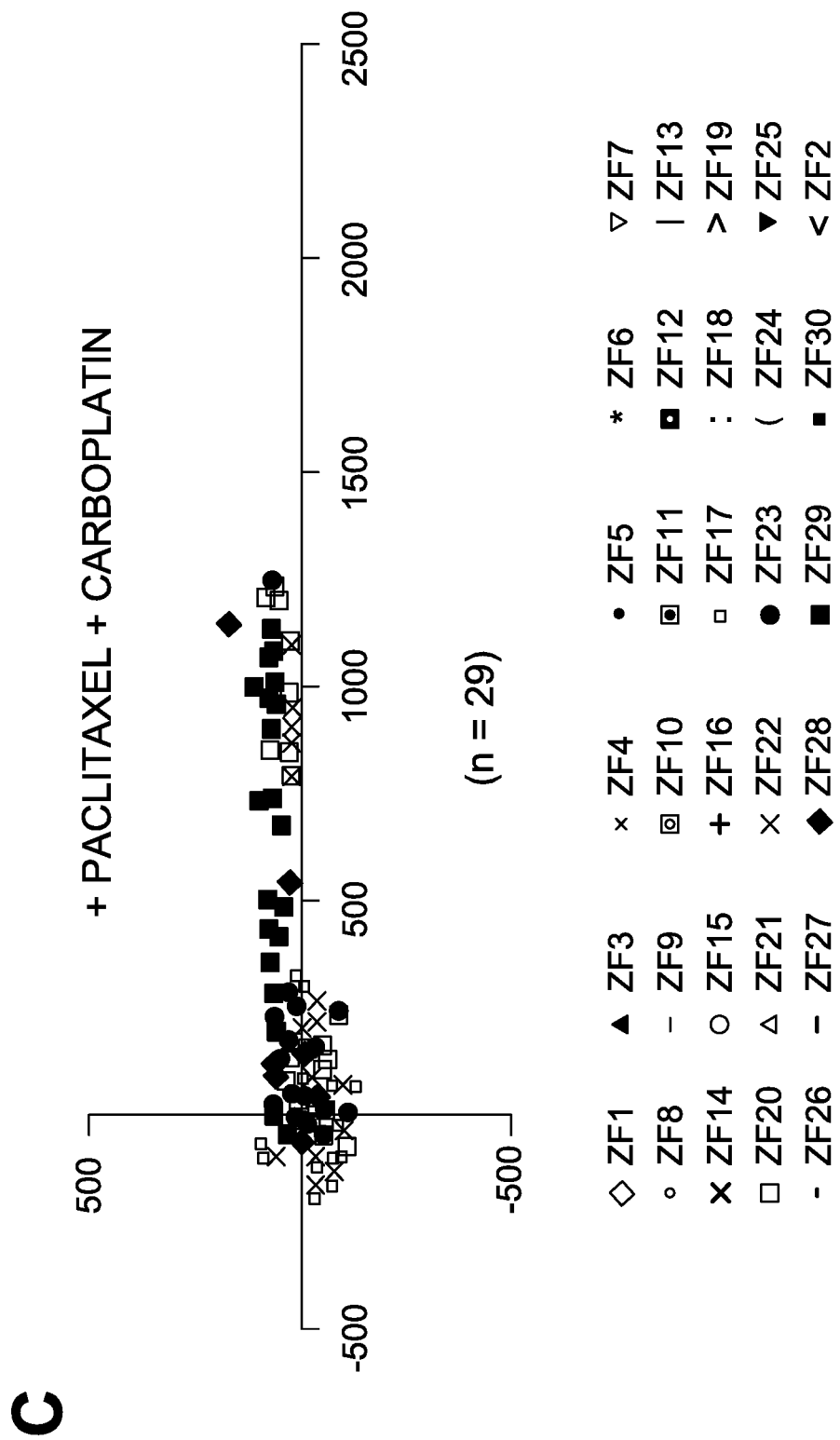
Figure 1:
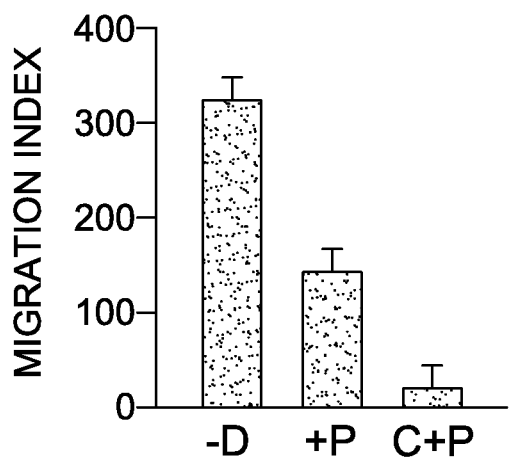
Figure 1:
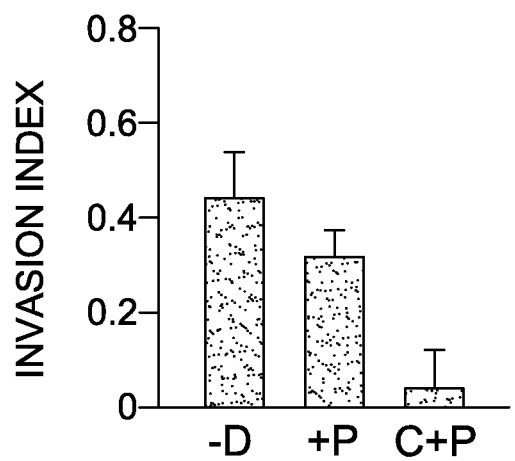
Figure 1:
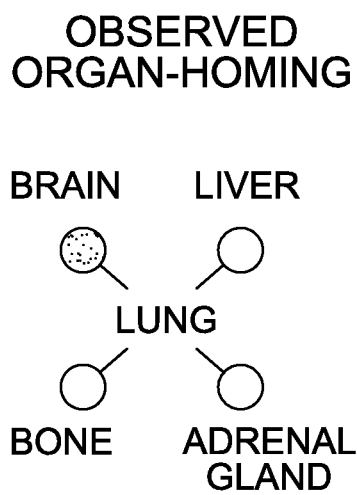
Figure 1:
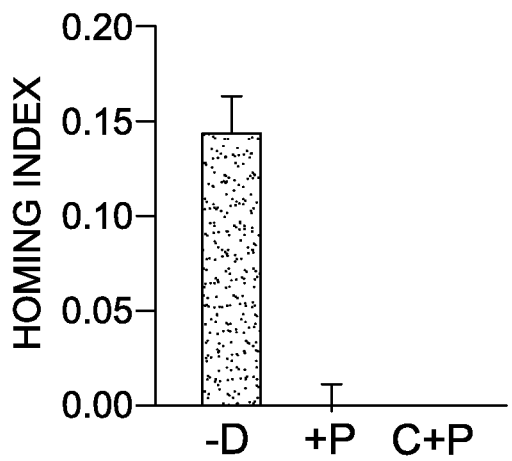

Molecular and genomic profiling of cancer cells has become the new trend in targeted therapy and oncology research. However, the relevance of molecular heterogeneity of the cancer cells and their constantly changing dynamic nature, the relevance of molecular signatures of the primary tumor as well invaded or metastasized tumor cells is limited. In this scenario, defined by limited efficacy of current chemotherapies to metastatic cancers, and the limited application of genomic profiling of cancer cells, we explored the possibility of creating representative and biologically relevant live 3D tumors out of tumor tissues (e.g., surgically removed primary tumor, biopsy, CTCs, etc.) to obtain clinically relevant physiological information about invasion and metastasis.

For a successful individualized and targeted approach to cancer treatment, a rapid assay method that can predict a patient's tumor physiology (such as growth, invasive ability, metastatic organ-homing, etc.) and response to various anti-cancer treatments is required.

An individualized and targeted treatment approach is however further complicated by the dynamic nature of all cancers. As a result every primary, invaded or metastasized tumor is made up of heterogeneous population of cells. Therefore a process of separating/fractionating the cancer cell pool into various physiological or molecular categories is important.

The present invention provides assays and methods for the prediction of cancer progression and response to treatment. The method may use an advanced "Cancer Progression and Response Matrix". Thus certain embodiments of the current invention may be used to facilitate the design of individualized and targeted therapies based on predictable tumor progression and responses to treatment.

Definitions

As used herein, the following terminologies have meanings ascribed to them unless specified:

"Subject" or "Patient" or "Individual" typically include humans but can also include other animals including but not limited to rodents, canines, felines, equines, ovines, bovines, porcines and primates.

"Tumor" includes a mass of cells found in or on the body of a subject that have some form of physiological, histological, molecular and or structural abnormality.

"Cancer" includes any member of a class of diseases that have abnormal cells which grow in an uncontrolled fashion. This includes all neoplastic conditions and all cancers whether characterized benign, invasive, localized, pre-metastatic, metastatic, post-metastatic, soft tissue or solid, including any stage or grade.

"Biology" or "Physiology" typically includes morphology, physiology, anatomy, behavior, origin, and distribution.

"Pathophysiology" all typically mean the disordered physiological processes associated with a condition. Particularly, cancer is a set of diseases that are driven by progressive genetic abnormalities that include chromosomal abnormalities, genetic mutations and epigenetic alterations. Particularly epigenetic alteration, which are functionally relevant modifications to the genome that does not involve a change in the nucleotide sequence, play a significant role in regulating the overall biology of cancer cells. Epigenetic alterations have been observed due to environmental exposures.

"Biopsy" refers to the process of removing cells or tissue samples for diagnostic or prognostic evaluation. Any known biopsy technique can be applied to the methods and compositions of present invention. Representative biopsy techniques include but are not limited to excisional, incisional, needle, and surgical biopsies. The choice of the biopsy technique used depends on tissue type to be evaluated and the location, size and type of the tumor.

"Invasion" refers to encroachment or intrusion. Particularly, invasive tumor cells are cells that are able to invade into surrounding tissues. Not all tumor cells have the ability to invade.

"Metastasis" is the development of secondary malignant growths ("Metastatic tumors") at a distance from a primary site of cancer. It is the spread of cancer cells from one organ or part of the body to another non-adjacent organ or part. Cancer cells first move into the circulatory system (intravasation) followed by positioning into a secondary site to create secondary tumors (extravasation).

"Circulating tumor cells" or "CTC" are tumor cells that have undergone intravasation and are found in the circulation. Circulating extratumoral cells include, but are not limited to, circulating tumor cells, disseminated cancer cells, and cancer stem cells. Circulating tumor cells can be otentially obtained from any accessible biological fluid such as whole blood, sputum, bronchial lavage, urine, nipple aspirate, lymph, saliva, needle aspirate, etc.

"Organ-homing" involves seeding of circulating tumor cells into organs of metastasis. Primary tumors tend to metastasize to specific distant "target" organs. For example, lung cancer tends to frequently metastasize to the brain. The process or organ selection is not a random process although the physiology behind organ-homing is not well understood.

"Signal transduction" occurs when an extracellular signaling molecule activates a cell surface receptor ("Signaling molecule" or "Signal transducer"). In turn, this receptor alters intracellular molecules creating a response, which typically include ordered sequences of biochemical reactions"

"Molecular genetic tumor markers" or "MGTMs" have been identified based on the biological characterization of tumors, such as tumor development, growth, invasion and metastasis. Some examples include, but are not limited to, oncogenes (K-ras, erbB-1 (EGFR), erbB-2 (HER-2/neu), bcl-2, c-/N-/L-myc, c-kit), tumor suppressor genes (p53, RB, p16, p27, FHIT, RASSF1A), telomerase, invasion and metastasis markers (MMP, VEGF, COX-2), cell adhesion factors (E-Cadherin, beta-catenin), epithelial markers (cytokeratin, CEA), apoptosis markers (caspase-3, cleaved PARP), single nucleotide polymorphism (SNP), and anticancer drug susceptibility markers (MRP, LRP, MDR, beta-tubulin, ERCC1). Differential activation/deactivation of signaling pathways as well as changes in invasiveness and/or organ-homing of cells, in presence of anticancer drugs can aid in the selection of a suitable cancer therapy regimen at the proper dose for each patient. There could be a multitude of related application including prediction of how well chemotherapy is progressing for a given patient.

"Chemicals" represents broadly all chemical compounds or substances that have been obtained crude, or have been purified from natural (available in nature through botanical or artificial sources (such as synthesized artificially in a laboratory).

"Synthesized or naturally occurring chemicals and biologicals" include, but are not limited to, medicinal or therapeutic substances, non-medicinal substances, occurring in nature, artificially created, preparations made from living organisms (plant, animal, etc.), or extracted from non-living animal sources or minerals. These can include chemotherapeutic drugs, pharmaceutical formulations, Natural Health Products, powders, tea and extracts, serums, vaccines, antigens, antitoxins, etc.

"Immunomodulation" is the adjustment of the immune responses, as in immunopotentiation (activation of the immune system), immunosuppression (suppression of the immune system), or induction of immunologic tolerance. Specifically, there is a complex dynamism between immune cells and malignant cells in the tumor microenvironment, which has there is in fact significant prognostic relevance as the immune system has both tumor promoting and inhibiting roles. Tumor infiltrating immune cells, and the chronic inflammation at the tumor site play a significant role in the growth, procession, invasion and metastatic disease. Immunomodulation can therefore impact greatly the progression of the disease. In the context of the current invention, immunomodulation therefore represents the adjustment of immune responses of the tumor infiltrating immune cells that came with the patient tumor cell mass, regulating the regulators of the immune systems (interleukins and interferons) and regulating the host immune system, specifically the zebrafish immune cells.

EXAMPLES OF THE INJECTION OF CIRCULATING TUMOR CELLS

Experiment 1: Injection of Breast Cancer Cell Line MDA-MB-231 in Zebrafish

Zebrafish eggs were collected and incubated for 48 h at 36 degC in E3 medium (5 mM NaCl. 0.17 mM KCl. 0.33 mM CaCl2. 0.33 mM MgSO4. 0.1% methylene blue). The embryos were anesthetized with tricaine and decorionated using Dumont #5 forceps.

MDA-MB-231 cells (metastatic breast cancer cells) were grown in D-MEM (high glucose), 10% fetal bovine serum (FBS), 0.1 mM MEM NonEssential Amino Acids (NEAA), 2 mM L-glutamine, 1% Pen-Strep and labelled using CM-DiI (Vibrant, Lifetech, 4 ng/ul final concentration, incubated 4 mM at 37° C. followed by 15 mM at 4° C.). 50 cells were injected into the yolk of one 48 hpf tricaine anesthetised zebrafish embryo. Images were taken 24 h post injection.

RESULTS: After injection, the isolated CTCs were localized at the site of injection but were also visible throughout the tail of the zebrafish embryo and were capable of forming metastatic patterns in the zebrafish embryo.

Experiment 2: Developing Tumors in Zebrafish from Isolated CTCs from Blood

CTCs were collected from 20 ml blood (EDTA-Ca as anti-coagulant) from a Stage 4 lung cancer patient who has metastasis in the brain and one control healthy individual. CTCs were collected by sequential positive (anti-EpCam BerP4 antibody, AbCaM) and negative (anti-CD45, AbCam) selections using antibody coated magnetic beads (Dynabeads, Lifetech) according to manufacturer's instructions. Two-capture-wash-release were performed for each step. The yield was about 110 cells from the metastasis patient but no cells were detectable from the healthy donor. The CTCs obtained were stained with DiO (Vibrant, Lifetech, 200 mM final concentration) for 20 min at 37 degC. Total of 100 stained CTC cells were injected into the yolk of one 48 hpf tricaine anesthetised zebrafish embryo. Images were obtained 24 h post injection. RESULTS: Isolated CTCs were capable of forming tumors and formed metastases in the brain tissues of the zebrafish larvae.

Experiment 3: Differential Response of Invasive and Non-Invasive Primary Lung Tumor Cells to Drugs Tumor tissues from late stage lung cancer patient that had shown metastasis to the brain was minced and incubated in Liberase DL (Roche) as per manufacturer's instructions. Lung cells were passed through a 70 micrometer cell strainer and resuspended in 2 ml RPMI 1640 before counting. Cell viability was confirmed by trypan blue exclusion. Cells are labeled with fluorescent tracking PKH-67 (Sigma) dye following the manufacturer's instructions and resuspended in PBS containing 25 mM glucose. 100 cells are injected into the yolk sac using NanojectII micromanipulator device. A group of embryos are injected with PBS+glucose only as control. The embryos are then incubated in TE water containing antibiotic/antimycotic solution and let to recover overnight in an incubator at 35 degC. After 24 h of incubation post tumor transplantation, embryos are imaged under a fluorescent microscope to ensure the presence of tumor cells in the yolk sac. Drugs/Treatments are added at various concentrations and the plate with embryos are incubated at 35° C. for an additional 3 days. Embryos were anesthetized with tricaine and re-imaged under a fluorescent microscope. Drugs used in this experiment were Paclitaxel alone or in combination with Carboplatin. Drug response was measured through expressions of 18 genes (BCL2, BCL-X, BCL-B, BFL-1, BCL-W, MCL1, CDC2, CYCLIN-D, CYCLIN-AL BAX, BAK, BOK, BID, BIM, BAD, BMF, NOXA, PUMA), nine (9) for survival (growth and cell cycle) and nine (9) for death (apoptosis).

RESULTS: Tumor coordinates graphically represented (FIG. 1) show very high reproducibility of the invasion and metastasis patterns in the presence or absence of drug treatment. There is differential response of the invasive tumors in comparison to non-invasive tumor cells in presence of drugs as measured through Invasion Index, Migration Index as well as Homing Index. There is also a very clear difference in survival (measured by cell cycle and growth) and death (measured by apoptosis) of non-invasive and invasive cells.

Examples of the Use of the Microinjection Apparatus

Description of FIGS. 2 to 5

As seen in the FIGS. 2 to 5, the multi-well plate assembly component 10 of one aspect of this invention includes a holding frame 12 including a base plate 28 supporting a plurality of embryo handling wells 24. In this embodiment, the assembly 10 is made in a 96 well plate format and complies with international standards, although other standards may be used. This set-up can therefore be used with all standard microtiter plate readers and can be manipulated in all suitable liquid handlers. The multi-well plate assembly component 10 includes a lid 16, which is preferably provided with labels to mark the positions of wells of the multi-well plate assembly component 10, that offers safety, isolation, and prevents liquid in wells from drying.

In this embodiment, eight separable, removable modules 18 (seen in detail in FIG. 3) are mounted in the holding frame 12. Every one of the eight separable, removable modules 18 has a groove plate 20 and a removable insert 22 that is mounted on the groove plate 20. As seen in FIG. 4, the groove plate 20 includes a plurality of the aforementioned embryo handling wells 24 and a lateral liquid handling well 26.

Each embryo handling well 24 preferably has a cylindrical upper section 30 and a conical lower section 32. The lateral liquid handling well 26 is preferably completely cylindrical. The lateral liquid handling well 26 and the embryo handling wells 24 are interconnected at their outlet ends by a transverse drain channel 34. The removable insert 22 abuts the holding frame 12 at its outer edge and abuts the outer edges of the embryo handling wells 24 at its lower edge. The removable insert 22 can be removed for better manipulation of the embryo. The mounting of the removable insert 22 does not need to be airtight as there is the above-described intercommunication between each embryo handling well 24. The base plate 28 should preferably be transparent and UV penetrable. The removable insert 22 may be colored.

Figure 2:
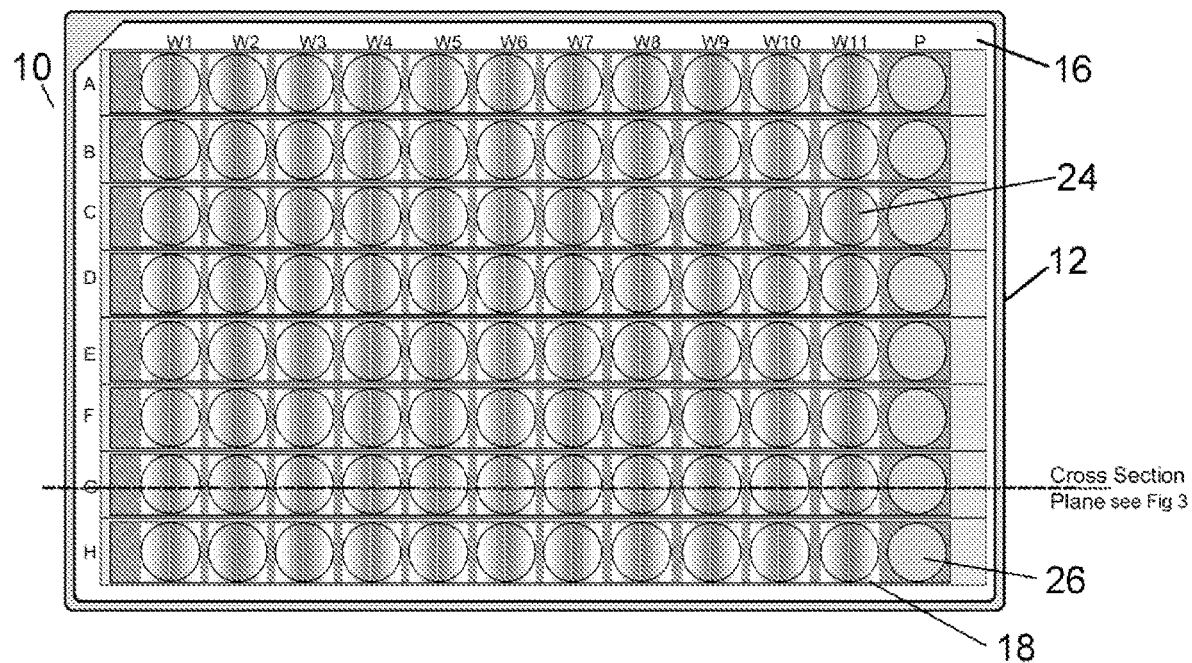
FIG. 2 is a top plan view of the multi-well plate assembly component of one aspect of this invention.
Figure 3:
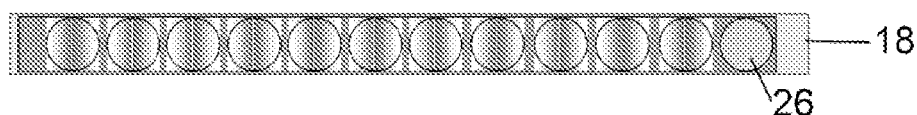
FIG. 3 is a top plan view of one of the removable modules of the embodiment of FIG. 2.
Figure 4:
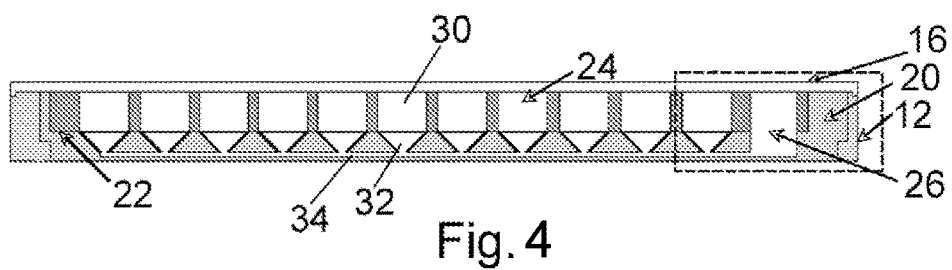
FIG. 4 is a cross section showing the embryos handling wells, with a groove plate sitting within the holding frame of the embodiment of FIG. 2.

In this embodiment as seen in FIGS. 2 to 4, there are 11 embryo handling wells 24 (W1-11) for housing embryos and one lateral liquid handling well 26. As previously described lateral liquid handling well 26 and the embryo handling wells 24 are interconnected at their outlet ends by a transverse drain channel 34. Therefore, any change in liquid level in one well (e.g. well W1) will result in compensation through other wells (e.g. wells W2 to W11). This will prevent uneven drying of wells and all wells will have the same liquid level. Therefore, all liquid handling, changing of media, etc. can be done by a robotic liquid handler in the liquid handling well 26, thereby substantially preventing handling, damage or stress to the embryos.

All manipulations are done on the groove plate 20. As previously described, the embryo handling wells 24 have a conical bottom 32 where the larva of the zebrafish can be placed. As will be seen later in FIGS. 6A and 6B, given the shape of the zebrafish larva, once anesthetized, they will fall into the well conical lower portion 32 of embryo handling well 24 with the yolk on top. As will be seen in FIG. 7, a cover plate 36 can be positioned over the groove plate 20 in the place of the removable insert 22. As will be seen in FIG. 7, this cover plate 36 can act as the guide for the injection of the tumor cells along with pro-angiogenic factors into the embryo.

Figure 5:
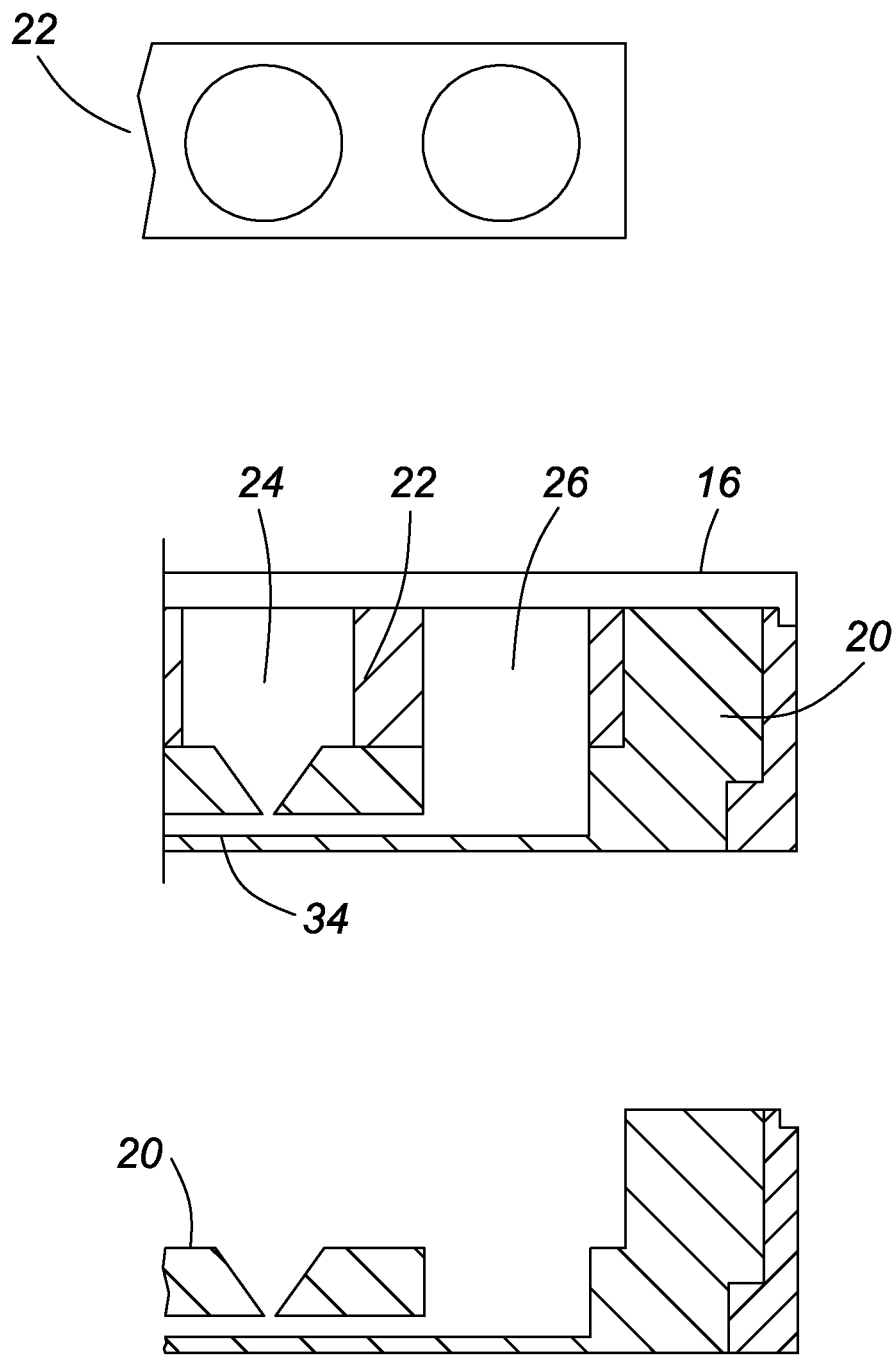
FIG. 5 is enlarged cross sections of the embryo handling wells and the removable insert of the embodiment of FIG. 2.

The rectangle area within the broken lines in FIG. 4 is shown in enlarged form in FIG. 5.

Description of FIGS. 6A and 6B

FIG. 6A is a horizontal transverse cross-section of a 48 hpf zebrafish embryo, and FIG. 6B is a vertical transverse cross-section of a 48 hpf zebrafish embryo.

Description of FIGS. 7 and 8

As seen in FIG. 7, a micropipette unit 40 may have a replaceable micropipette, 42, preferably of glass. The 48 hpf zebrafish embryo 48 is disposed in the conical lower section 32 of the embryo handling well 24, with its dorsal side 50 within the lower narrower end of the conical section 32 and with its yolk 52 in the upper wider end of the conical section 32. The unit so provided is protected by the cover plate 36. The micropipette unit 40 is positioned to inject the tumor cells along with pro-angiogenic factors, preferably growth factor angiopoietin into the yolk 52 through the aperture in the cover plate 38.

As seen in FIG. 8, the micropipette unit 40 having the replaceable micropipette 42 is controlled by a robotic arm 54. The liquid solution of the tumor cells along with a pro-angiogenic factor, preferably growth factor angiopoietin, is conducted through the robotic arm 52 via conduit 56. The robotic injector arm 54 can be rotated at any angle by means of control arm 58. The rotation is shown schematically by arrows 60.

Figure 9:
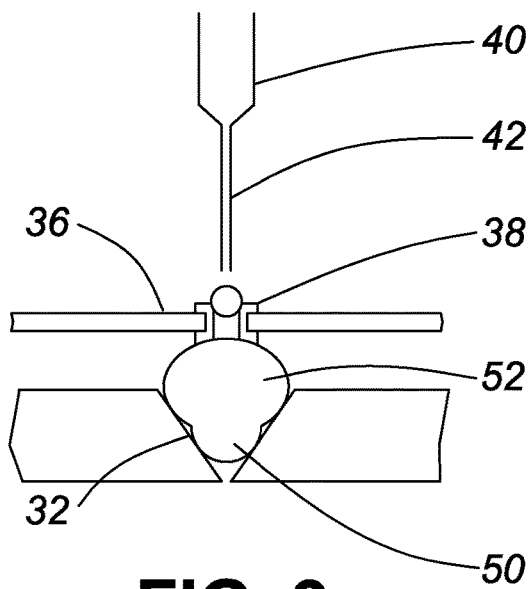
FIG. 9 is a schematic side view of a 48 hpf zebrafish embryo in a groove plate with an injection cover plate as a guide for the micropipette for microinjection of a tumor into a 48 hpf zebrafish embryo according to an embodiment of this invention.
Figure 10:
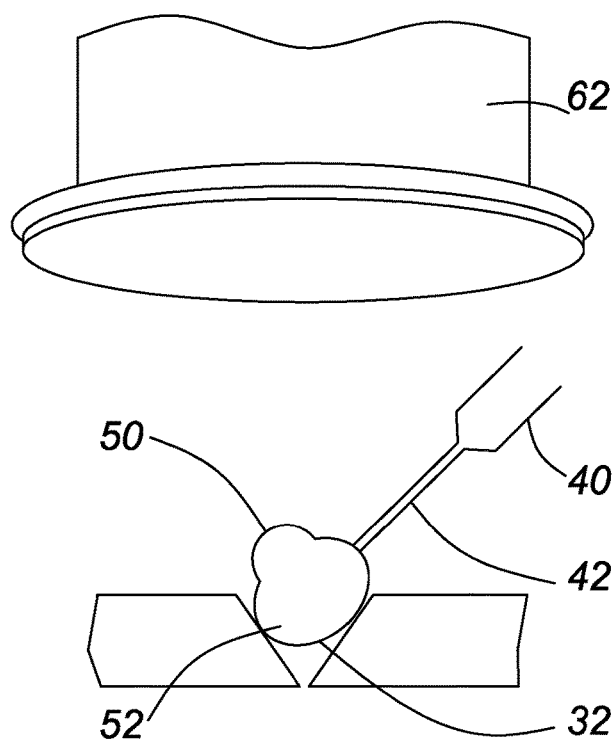
FIG. 10 is a schematic side view of a 48 hpf zebrafish embryo in a groove plate showing the rotatable angle of the micropipette for microinjection while the embryo is in the groove plate according to an embodiment of this invention.

Description of FIGS. 9, 10 and 11

FIG. 9 is a simplified replication of FIG. 7 showing the use of the cover plate 36 as a guide for the injection of the tumor along with a pro-angiogenic factor, preferably growth factor angiopoietin, into the yolk 52.

As seen in FIG. 10, manipulations can be done under a microscope 62 without the removable insert in place. This allows manipulation of the embryo at any angle and injection can be performed to any part of the embryo body 50, 52.

Figure 11A:
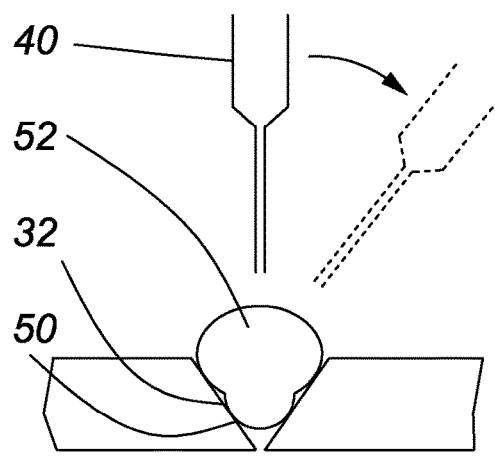
FIG. 11A and FIG. 11B are schematic side views of a 48 hpf zebrafish embryo in a groove plate showing the flexibility for rotation of the micropipette while still allowing access to the embryo in the groove plate for microinjection thereinto according to an embodiment of this invention.

As seen in FIG. 11A, the micropipette unit 40 can be rotated from a vertical position shown in solid lines to a tilted position shown in broken lines so that injection can be performed to any part of the embryo body 50, 52.

Figure 11B:
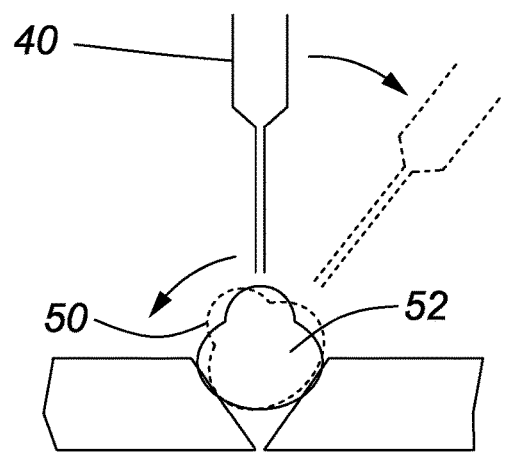

As seen in FIG. 11B, the micropipette unit 40 can be rotated from a tilted position shown in solid lines to a vertical position shown in broken lines so that injection can be performed to any part of the embryo body 50, 52. FIG. 8B also shows that the embryo body 50, 52 can also be rotated.

Process of Operation

Embryos are dechorionated at 48 hpf and moved to wells using a glass pipette. If desired, embryos can be treated with pro-angiogenic factor, preferably growth factor angiopoietin, to increase the likelihood and efficiency of tumor cell uptake. Media is removed partially through well 36 and tricaine is added to anesthetize the embryos. Tricaine solution can be added to each well 24 as well to speed up the process. The embryos undergo anesthesia and fall to the lower conical bottoms 32 of the embryo handling wells 24 of the groove plates 20. Given the conical shape 32 at the bottom of the embryo handling wells 24, and the yolk 52 being lighter than the rest of the body 50, larvae fall with yolk 52 facing upwardly. If required, injection cover plate 36 can be positioned to guide the tumor cell along with the pro-angiogenic factor, preferably growth factor angiopoitin. Robotic arm 54 fitted with the glass micropipette 40 is used to inject the tumor cells along with the pro-angiogenic factor, preferably growth factor angiopoietin, into the embryo yolk 50. The yolk sac seals itself rapidly.

Once injections are complete, the injection cover plate 36 is removed and the removable insert 22 is positioned to create the wells 24.

Pipetting out tricaine solution through well 26 can change the fluids in the wells 24, and fresh media is added again through well 26. The wells 24 for each row of 11 embryos will therefore be filled, and each embryo will revive from anesthesia. Once they revive, they are free to swim around in their own wells and not mix with neighbouring embryos. This allows keeping track of individual embryos. The entire assembled unit with the lid 16 on and with swimming zebrafish larvae inside, can be stacked one above another and stored in an incubator as for other microtiter plates.

Since, preferably, the groove plate 20 is transparent, the larvae can be observed under UV in real time without needing to handle the larvae. If needed, larvae can be anesthetized for observations as mentioned earlier without handling them. Not only tumor growth can be measured using software, but also swimming behavior can be observed in real time. Such observations may alternatively be done manually or by using detection software.

After carrying out the above described example experiments, if the larvae need to be euthanized and stained, all handling of the larvae and changing of liquids can be done in this plate. One of the most important steps in whole embryo staining is rocking and shaking of embryos in solution for proper mixing.

This step is generally performed in Eppendorf tubes because the mixing is not good in most 96 well plates even on a shaker. By pipetting up and down in well 26 alone, all 11 embryos can be rocked and shaken on a single module. Similarly, using a programmed liquid handler, all such processes for the entire plate can be optimized.

Once all staining is done, fluorescence as a measure of tumor mass can be calculated directly using a UV plate reader. This same equipment can be used for other injections, such as DNA, RNA, morpholinos as well.

What is claimed is:

1. A method to establish tumors from circulating tumor cells (CTCs) obtained from biopsies for analysis of said CTCs comprising the steps of:
   (a) isolating one or more of said CTCs;
   (b) labeling the one or more CTCs with a cell tracking dye;
   (c) injecting the one or more CTCs into a 24 to 48 hours post fertilization (hpf) zebrafish embryo ("embryo"), having an embryo body and an embryo yolk sac;
   (d) incubating the embryo for 24 hours or more;
   (e) establishing one or more tumors in the embryo; and optionally repeating steps (c) trough (e) for multiple embryos.

2. The method of claim 1, wherein the cell tracking dye is a fluorescent dye.

3. The method of claim 1, wherein the one or more CTCs are injected into a 24 to 48 hpf zebrafish embryo yolk sac.

4. The method of claim 3, further comprising measuring a position of each of the one or more injected CTCs after incubating the embryo to determine whether the injected CTCs invade the embryo body or remain in the 24 to 48 hpf zebrafish embryo yolk sac.

5. The method of claim 4, further comprising using the position of at least one injected CTC to measure CTC metastatic potential, wherein if the at least one injected CTC invades the embryo body, the at least one injected CTC has metastatic potential.

6. The method of claim 4, wherein each position is measured by capturing one or more fluorescence images of the injected CTCs under a fluorescence microscope.

7. The method of claim 6, further comprising quantitating the injected CTCs in the 24 to 48 hpf zebrafish embryo yolk sac and the embryo body by one or more of:
   (a) using image analysis software to measure a width and a length of a CTC focus and calculate a volume of the CTC focus as $\frac{1}{2}(width)(length)^2$, wherein each tumor comprises a CTC focus and contains at least one of the injected CTCs;
   (b) measuring an invasive index (II) of the CTC foci as II=$1/n \ \Sigma$(number of CTC foci in the embryo at T hours/total number of CTCs injected in the embryo), where n is the number of embryos in the experiment, and T is the incubation time, and the greater the II, the higher the propensity of the injected CTCs to invade; and
   (c) measuring a migration index (MI) of the CTCs as MI=$1/n \ \Sigma$(CD at T hours/total number of CTC foci at time T hours), where CD=Cumulative distance traveled by the injected CTCs, n is the number of embryos in the experiment, and T is the incubation time, where the higher the value of the MI, the more aggressively invasive are the injected CTCs.

8. The method of claim 7, further comprising determining whether any one of: the volume of the CTC focus; the II; or the MI are different in the presence versus the absence of a chemical.

9. The method of claim 1, wherein a first embryo incubation is with a chemical and a second embryo incubation is without the chemical, and the first embryo incubation is compared to the second embryo incubation.

10. The method of claim 9, further comprising measuring an effect of the chemical on the injected CTCs by:
   (a) digesting the first embryo and the second embryo in a protease solution after incubation to obtain injected CTCs;
   (b) dispersing the embryo and the injected CTCs with pipetting to dissociate them to one or more single cell suspensions;
   (c) fixing and counting the viable injected CTCs in the one or more single cell suspensions under a fluorescence microscope;
   (d) calculating a ratio of the viable injected CTCs to the injected CTCs;
   (g) comparing the ratio for incubation in the presence of the chemical to the ratio for incubation in the absence of the chemical; and
   (f) using the comparison to determine whether the chemical affects the injected CTCs.

11. The method of claim 9, further comprising measuring and comparing a pattern of invasiveness of the injected CTCs in the presence or absence of the chemical.

12. The method of claim 1, further comprising assessing changes in CTC DNA by:
(a) enzymatically digesting the embryo and the injected CTCs after incubation;
(b) isolating DNA from the digested embryo and the injected CTC;
(c) PCR amplifying one or more genes from a first aliquot of the isolated DNA;
(d) sequencing the PCR amplified one or more genes; and
(e) bisulfite sequencing a second aliquot of the isolated DNA to locate one or more epigenetic modifications.

13. The method of claim 1, further comprising analyzing CTC gene expression by:
(a) enzymatically digesting the embryo and the injected CTC after incubation;
(b) isolating RNA from the digested embryo and the injected CTC; and
(c) performing a Quantitative Real-Time PCR analysis of the CTC gene expression using two or more primers designed for one or more human genetic sequences.

14. The method of claim 1, further comprising analyzing a CTC protein expression by one or more of:
(a) fixing the embryo using a chemical fixative;
(b) using immunohistochemistry with one or more human protein antibodies to visualize the CTC protein expression;
(c) visualizing the CTC protein expression using immunohistochemistry on one or more histological section slides of the embryo after CTC injection and incubation;
(d) visualizing the CTC protein expression using an ELISA (enzyme-linked immunosorption assay); and
(e) visualizing the CTC protein expression using a Western blot.

15. The method of claim 1, wherein a pro-angiogenic factor is added into water containing the zebrafish embryo before, during or after the injection of the CTCs.

16. The method of claim 15, wherein the pro-angiogenic factor is angiopoietin.

17. The method of claim 1, further comprising:
(a) capturing one or more fluorescence images of the injected CTCs under a fluorescence microscope using green and red fluorescence filters after incubating the embryo;
(b) analyzing the one or more fluorescence images using an image analysis software to capture a position of each of one or more CTC foci in the one or more fluorescence images, wherein each tumor comprises a CTC focus and contains at least one of the injected CTCs; and
(c) using the analysis of the one or more fluorescence images to calculate a homing index (HI) of the CTCs as: $HI=1/n\ \Sigma$(total number of CTC foci in an organ at T hours/total number of CTC foci at time T hours), where n is the number of embryos considered in the experiment, and T is the incubation time T;
wherein (i) the cell tracking dye has a red fluorescence and (ii) the CTCs are injected into a 24 to 48 hpf green fluorescent protein transgenic zebrafish embryo yolk.

18. The method of claim 17, further comprising observing an organ-homing pattern change of the injected CTCs in the absence versus the presence of a drug.

* * * * *